United States Patent
Conklin (10) Patent No.: US 9,149,360 B2
(45) Date of Patent: Oct. 6, 2015

(54) DYNAMIC ANNULOPLASTY RING SIZER

(71) Applicant: Edwards Lifesciences Corporation, Irvine, CA (US)

(72) Inventor: Brian S. Conklin, Orange, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 16 days.

(21) Appl. No.: 14/187,084

(22) Filed: Feb. 21, 2014

(65) Prior Publication Data

US 2014/0277421 A1 Sep. 18, 2014

(51) Int. Cl.
*A61F 2/24* (2006.01)
*A61B 5/107* (2006.01)
*A61B 19/00* (2006.01)

(52) U.S. Cl.
CPC .............. *A61F 2/2496* (2013.01); *A61B 5/107* (2013.01); *A61B 5/1076* (2013.01); *A61B 19/46* (2013.01); *A61F 2/2445* (2013.01); *A61F 2/2472* (2013.01)

(58) Field of Classification Search
CPC .... A61B 5/107; A61B 5/1072; A61B 5/1076; A61B 19/46; A61F 2/2496
See application file for complete search history.

(56) References Cited

U.S. PATENT DOCUMENTS

| | | | |
|---|---|---|---|
| 4,211,241 A | 7/1980 | Kaster et al. | |
| 4,643,194 A | 2/1987 | Fogarty | |
| 5,042,161 A | 8/1991 | Hodge | |
| 5,360,014 A | 11/1994 | Sauter et al. | |
| 5,489,296 A | 2/1996 | Love et al. | |
| 5,814,098 A | 9/1998 | Hinnenkamp et al. | |
| 5,885,228 A | 3/1999 | Rosenman et al. | |
| 6,019,739 A | 2/2000 | Rhee et al. | |
| 6,042,554 A | 3/2000 | Rosenman et al. | |
| 6,110,200 A | 8/2000 | Hinnenkamp | |
| 6,210,338 B1 | 4/2001 | Afremov et al. | |
| 6,319,281 B1 | 11/2001 | Patel | |
| 6,350,281 B1 | 2/2002 | Rhee | |
| 6,582,419 B1 | 6/2003 | Schoon et al. | |
| 6,598,307 B2 | 7/2003 | Love et al. | |
| 6,846,324 B2 | 1/2005 | Stobie | |
| 7,007,396 B2 | 3/2006 | Rudko et al. | |

(Continued)

FOREIGN PATENT DOCUMENTS

WO 9640006 A1 12/1996
WO 9725003 A1 7/1997

(Continued)

*Primary Examiner* — Max Hindenburg
(74) *Attorney, Agent, or Firm* — Pui Tong Ho; AnneMarie Kaiser; Guy Cumberbatch (57) ABSTRACT

A dynamic, adjustable annuloplasty ring sizer can include an adjustable ring replica, which can be adjusted through a range of sizes corresponding to available prosthetic annuloplasty repair ring sizes. Actuation of an adjustment trigger on a handle portion of the ring sizer can displace tension wires that extend through a malleable shaft and through a plurality of articulating segments that form the ring replica. Displacement of the tension wires causes flexion of the joints between adjacent articulating segments, thereby reducing the overall size of the ring replica. Releasing the tension wires can allow an elastic extension wire to act on the ring replica, enlarging the ring replica to its maximum, at-rest size. In this manner, the appropriate size of annuloplasty ring prosthesis can be determined with a single device, without requiring a plurality of static ring sizers that require individual insertion and placement for the conventional trial-and-error sizing methods.

19 Claims, 10 Drawing Sheets

(56) References Cited

U.S. PATENT DOCUMENTS

| | | |
|---|---|---|
| 7,258,698 B2 | 8/2007 | Lemmon |
| 7,510,573 B2 * | 3/2009 | Gabbay .................. 623/2.11 |
| 7,713,216 B2 | 5/2010 | Dubey et al. |
| 8,057,396 B2 | 11/2011 | Forster et al. |
| 8,449,625 B2 | 5/2013 | Campbell et al. |
| 8,728,013 B2 * | 5/2014 | Perle et al. ................ 600/591 |
| 8,874,203 B2 * | 10/2014 | Kassab et al. ............. 600/547 |
| 9,005,139 B2 * | 4/2015 | Klaiman et al. ........... 600/587 |
| 2002/0020074 A1 | 2/2002 | Love et al. |
| 2004/0237321 A1 | 12/2004 | Rudko et al. |
| 2006/0195134 A1 | 8/2006 | Crittenden |
| 2007/0299513 A1 | 12/2007 | Ryan et al. |
| 2009/0192600 A1 | 7/2009 | Ryan |
| 2009/0192602 A1 | 7/2009 | Kuehn |
| 2009/0192603 A1 | 7/2009 | Ryan |
| 2009/0192604 A1 | 7/2009 | Gloss |
| 2009/0192605 A1 | 7/2009 | Gloss et al. |
| 2010/0152844 A1 | 6/2010 | Couetil |
| 2010/0249661 A1 | 9/2010 | Righini et al. |

FOREIGN PATENT DOCUMENTS

| | | |
|---|---|---|
| WO | 9741801 A1 | 11/1997 |
| WO | 2010111621 A1 | 9/2010 |
| WO | 2011106354 A1 | 9/2011 |

* cited by examiner

DYNAMIC ANNULOPLASTY RING SIZER

RELATED APPLICATIONS

The present application claims priority under 35 U.S.C. §119(e) to Provisional Application No. 61/778,086, filed on Mar. 12, 2013.

FIELD

The present invention relates generally to medical devices and particularly to a dynamic annuloplasty ring sizer.

BACKGROUND

Figure 1:
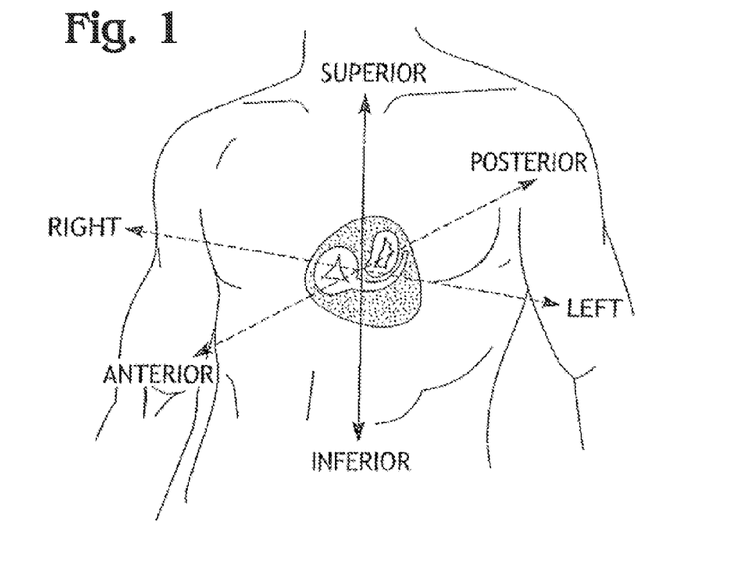
FIG. 1 is a schematic representation of the AV junctions within the heart and the body in the left anterior oblique projection.

In vertebrate animals, the heart is a hollow muscular organ having four pumping chambers: the left and right atria and the left and right ventricles, each provided with its own one-way valve. The native heart valves are identified as the aortic, mitral (or bicuspid), tricuspid, and pulmonary, and each is mounted in an annulus comprising dense fibrous rings attached either directly or indirectly to the atrial and ventricular muscle fibers. Each annulus defines a flow orifice. FIG. 1 shows a schematic representation of the anatomic orientation of the heart, illustrating the atrioventricular (AV) junctions within the heart and the body in the left anterior oblique projection. The body is viewed in the upright position and has three orthogonal axes: superior-inferior, posterior-anterior, and right-left.

Figure 2:
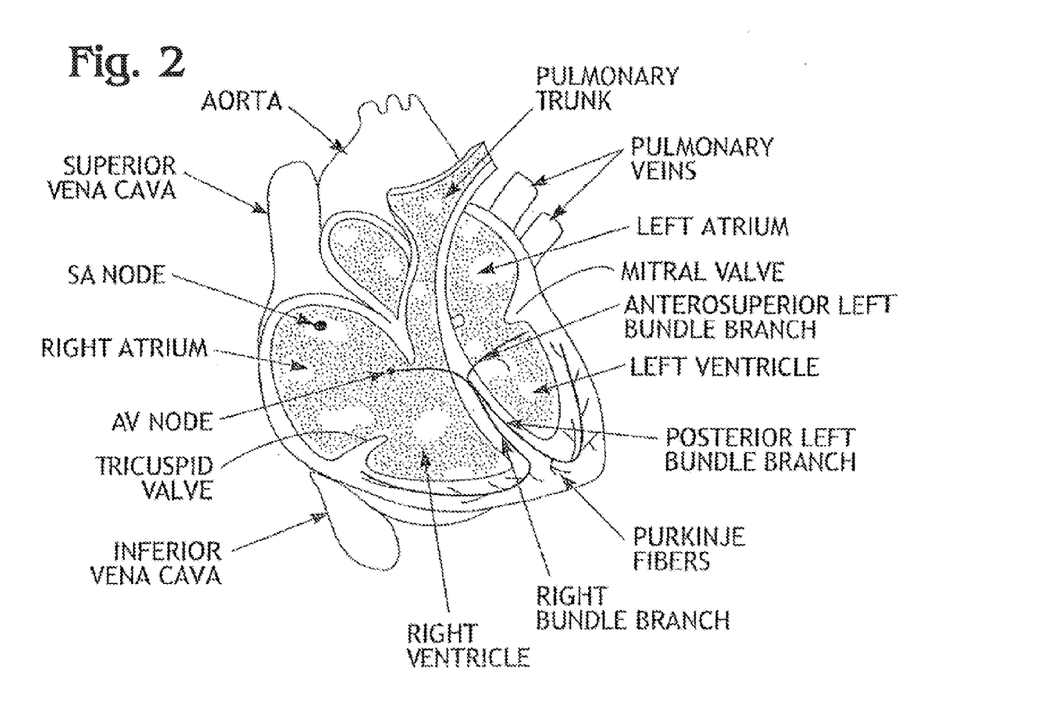
FIG. 2 is a cutaway view of the heart from the front, or anterior, perspective.

FIG. 2 is a cutaway view of the heart from the front, or anterior, perspective, with most of the primary structures marked. As is well known, the pathway of blood in the heart is from the right atrium to the right ventricle through the tricuspid valve, to and from the lungs, and from the left atrium to the left ventricle through the mitral valve. The present application has particular relevance to the repair of the mitral valve, which regulates blood flow between the left atrium and left ventricle, although certain aspects may apply to repair of other of the heart valves. The tricuspid and mitral valves together define the AV junctions.

Heart valve disease is a widespread condition in which one or more of the valves of the heart fails to function properly. Diseased heart valves may be categorized as either stenotic, wherein the valve does not open sufficiently to allow adequate forward flow of blood through the valve, and/or incompetent, wherein the valve does not close completely, causing excessive backward flow of blood through the valve when the valve is closed (regurgitation). Valve disease can be severely debilitating and even fatal if left untreated.

Various surgical techniques may be used to repair a diseased or damaged valve. In a valve replacement operation, the damaged leaflets are excised and the annulus sculpted to receive a replacement valve. Another less drastic method for treating defective valves is through repair or reconstruction, which is typically used on minimally calcified valves. One repair technique is remodeling annuloplasty, in which the deformed valve annulus is reshaped by attaching a prosthetic annuloplasty repair segment or ring to the valve annulus. The annuloplasty ring is designed to support the functional changes that occur during the cardiac cycle: maintaining coaptation of the valve leaflets and valve integrity to prevent reverse flow while permitting good hemodynamics during forward flow. Annuloplasty ring repair is currently performed on both mitral and tricuspid valves, through both traditional surgical procedures as well as minimally invasive approaches.

An annuloplasty ring typically comprises an inner substrate of a metal such as rods or bands of stainless steel or titanium, or a flexible material such as silicone rubber or Dacron cordage, covered with a biocompatible fabric or cloth to allow the ring to be sutured to the fibrous annulus tissue. Annuloplasty rings may be stiff or flexible, split or continuous, and may have a variety of shapes, including circular, D-shaped, C-shaped, or kidney-shaped. Examples are seen in U.S. Pat. Nos. 5,041,130, 5,104,407, 5,201,880, 5,258,021, 5,607,471, 6,187,040, and 6,908,482. Annuloplasty rings are available in a variety of different sizes to accommodate differences in the sizes of patients' native valves. The correct size of prosthetic annuloplasty ring to use for a given patient must be determined for each repair procedure performed.

To perform successful valve replacement or annuloplasty surgeries, the size of the valve annulus must be accurately measured. In conventional methods, sizing may be achieved by measuring the width and height of the anterior leaflet of the mitral valve, for example, by using a valve sizer or template, which resembles the shape of the annulus and is provided in various incremental sizes corresponding to the stepped valve or repair ring sizes. In order to use a sizing template, a surgeon or other user estimates the valve annulus size and selects the template accordingly. The template is guided into proximity of the annulus with a handle. If the template is judged to be the incorrect size, it is withdrawn, and replaced by a different template. Once the size of the annulus has been determined, a properly sized valve or annuloplasty repair ring is selected and implanted.

Thus, during a heart valve repair procedure, the size of a patient's native heart valve annulus is typically determined by holding various sizers adjacent the native annulus, where each of the various sizers represents an available prosthetic repair ring device size. The surgeon then determines which of the sizers is closest to the patient's native annulus, generally with a best guess visual determination of which sizer looks "correct." A surgeon typically must try several different sizers, sometimes more than once, and perhaps even test one or more repair ring sizes before being able to determine the correct repair ring size for a given patient. This trial-and-error sizing technique is imprecise, tedious, and time-consuming. Furthermore, the surgical field may be cluttered with several different static sizers.

Less invasive annuloplasty procedures have been developed in recent years, but traditional annuloplasty and valve sizing and holding instruments are designed for use with open-chest surgery that exposes the implant site. Currently, sizers are dimensionally the same as the repair rings they represent. Because of this, it can be difficult to insert the sizers through minimally invasive surgical incisions, such as thoracotomies. Inserting several sizers, one at a time, through a small incision can be particularly time-consuming and frustrating for surgeons.

Thus, for these and other reasons, there remains a need for an improved sizer and method of sizing a patient's valve annulus for annuloplasty repair.

SUMMARY

It is desirable to have a single, adjustable sizer that could be used to quickly and accurately determine the appropriate repair ring size for a given patient's heart through a minimally sized incision. Adjustable sizers according to the present disclosure can be collapsible and adjustable through the entire range of repair ring device sizes and display the selected size on the handle of the device. Disclosed embodiments of a ring sizer can allow for determination of the appropriate size of prosthetic annuloplasty ring without needing multiple ring sizers, and without needing to insert and withdraw multiple ring sizers through a minimally invasive entry. Disclosed embodiments of adjustable ring sizers can thus reduce the trial-and-error nature of repair ring sizing techniques, as well as reduce clutter in the surgical field, and reduce the time required for surgery and/or bypass. Some embodiments of an adjustable ring sizer can be collapsible for insertion through a small incision as part of a minimally invasive surgical procedure.

Disclosed embodiments of such a ring sizer can generally include a dynamic, adjustable ring replica at the distal end of the ring sizer, with the ring replica being adjustable through a range of sizes corresponding to available prosthetic device sizes. A user can thus determine the appropriate size of, for example, an annuloplasty ring for a particular patient or procedure using a single device, by manipulating the handle to adjust the size of the adjustable ring replica until the appropriate size is determined.

For example, in one particular embodiment, an adjustable annuloplasty ring sizer can include a device body having a proximal end and a distal end, a handle portion positioned adjacent the proximal end of the device body, an adjustable annuloplasty ring replica positioned adjacent the distal end of the device body, and a shaft that couples the adjustable ring replica to the handle portion of the ring sizer device body. The adjustable ring replica can be configured to be adjusted to a plurality of different sizes. In some embodiments, the shaft is a malleable shaft comprising a hollow bore configured to receive at least one elongated member configured to adjust the adjustable ring replica to a plurality of different sizes. For example, the shaft can be configured to receive one or more wires or cables that extend from the handle portion to the adjustable ring replica. Manipulation of the handle portion can in turn adjust the size of the adjustable ring replica by virtue of the elongated members (which can be, for example, sutures, wires, braided cables, and/or wire rope).

In some embodiments, the handle portion can include an adjustment trigger, and actuation of the adjustment trigger can be configured to expand and contract the adjustable ring replica. For example, actuation of the adjustment trigger can be configured to displace or release at least one elongated member, which can in turn reduce or enlarge the size of the ring replica.

The adjustable ring replica can be a generally C-shaped ring replica having a first free end and a second free end, as well as an inner surface and an outer surface. In some embodiments, the adjustable ring replica can comprise a plurality of articulating segments, wherein each of the articulating segments is moveable with respect to one or more respective adjacent articulating segments. In some embodiments, the adjustable ring replica can include an elongated backbone segment having a first backbone end and a second backbone end, wherein a plurality of articulating segments can be serially arranged and coupled to the first backbone end and extend to the first free end of the adjustable ring replica. Likewise, a plurality of articulating segments can be serially arranged and coupled to the second backbone end and extend to the second free end of the adjustable ring replica. Thus the elongated backbone segment can essentially serve as a central portion of the C-shaped ring replica, and can be positioned approximately equidistant from the first and second free ends of the ring replica. Further, the elongated backbone segment can be coupled to the shaft, such as by, for example, an articulating joint (e.g., a ball-and-socket joint).

The adjustable ring replica can include at least two bores, or channels, extending through the articulating segments and the elongated backbone segment. For example, in one embodiment, the adjustable ring replica can include an extension wire channel and a tension wire channel. In one embodiment, the extension wire channel can be positioned adjacent the outer surface of the adjustable ring replica and the tension wire channel can be positioned near the center of the articulating segments, or adjacent the inner surface of the adjustable ring replica.

In some embodiments, the extension wire channel is configured to receive at least one elongated member, which can be an elastically deformable material that extends from the first free end of the adjustable ring replica to the second free end of the adjustable ring replica. Similarly, the tension wire channel can be configured to receive at least one elongated member. In some embodiments, the tension wire channel can be configured to receive a first elongated member extending from the elongated backbone segment to the first free end of the adjustable ring replica and a second elongated member extending from the elongated backbone segment to the second free end of the adjustable ring replica.

Displacement of the tension wires (e.g., by actuation of the adjustment trigger on the handle portion of the sizer) can create a moment about a pivot area between adjacent articulating segments, which in turn can result in flexion of the joint between adjacent articulating segments, thereby reducing the overall diameter of the ring replica. When tension is released on the elongated members extending through the tension wire channel, the extension wire (e.g., the elongated member extending through the extension wire channel) can be configured to cause expansion of the ring replica back to the maximum, at-rest ring size. The ring replica can thereby be adjusted through a range of sizes corresponding to available prosthetic annuloplasty rings. The adjustable annuloplasty ring sizer can be manipulated at an implant site until the correct prosthesis size is determined, without the need to remove or insert multiple ring sizers, as is the case with conventional methods.

One specific embodiment of a sizing device for selecting the correct repair ring size to use in a given surgical procedure, can include a handle portion positioned adjacent a proximal end of the device, an adjustable C-shaped ring replica positioned adjacent a distal end of the device, wherein the adjustable C-shaped ring replica can include a free ring end and a second free end, a malleable shaft coupling the handle portion to the adjustable C-shaped ring replica via an articulating joint, the malleable shaft being configured to receive at least one tension wire, and an adjustment trigger positioned adjacent the handle portion, wherein actuation of the adjustment trigger can be configured to displace the at least one tension wire, and wherein displacement of the at least one tension wire can be configured to contract and/or expand the adjustable C-shaped ring replica.

Further, the C-shaped adjustable ring replica can include a backbone segment coupled to the malleable shaft, wherein the backbone segment includes a first backbone end and a second backbone end opposite the first backbone end, wherein a first plurality of articulating segments serially coupled to one another extend in an elongated manner from the first backbone end to the first free end of the ring replica, and wherein a second plurality of articulating segments serially coupled to one another extend in an elongated manner from the second backbone end to the second free end of the ring replica. In this embodiment, the C-shaped adjustable ring replica can include an extension wire channel adjacent an outer ring surface and a tension wire channel adjacent an inner ring surface, and displacement of the at least one tension wire can be configured to move each respective articulating segment with respect to each adjacent articulating segment and/or the backbone segment. In some embodiments, the ring sizer can further include a display on the handle portion of the device, wherein the display can be configured to provide the size of annuloplasty ring that corresponds to each respective size of the adjustable ring replica. For example, if an embodiment of an adjustable ring sizer has a range of 24-40 mm, the display window can be configured to read "24" or "24 mm" or the like, when the ring replica is in its contracted, minimal configuration (e.g., when maximum tension is placed on the tension wires and the ring replica is contracted to a size that corresponds to a repair ring size of 24). Likewise, the display window can be configured to read "40" or "40 mm" or the like when the ring replica is in its expanded, maximum configuration (e.g., when tension is released from the tension wires and the ring replica is allowed to expand to a size that corresponds to a repair ring size of 40). The display window can be configured to display the size within the range that corresponds to the present size of the ring replica. Thus, the display can change through a plurality of available repair ring sizes as the size of the ring replica is adjusted (e.g., expanded and contracted via manipulation of the adjustment trigger) between the minimum and maximum configurations.

The foregoing and other objects, features, and advantages of the invention will become more apparent from the following detailed description, which proceeds with reference to the accompanying figures.

DETAILED DESCRIPTION

As used in this application and in the claims, the singular forms "a," "an," and "the" include the plural forms unless the context clearly dictates otherwise. Additionally, the term "includes" means "comprises." Although the operations of exemplary embodiments of the disclosed method may be described in a particular, sequential order for convenient presentation, it should be understood that the disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed herein. Moreover, for the sake of simplicity, the attached figures may not show the various ways in which the disclosed system, method, and apparatus can be used in combination with other systems, methods, and apparatuses.

Embodiments of a heart valve repair ring sizer according to the present disclosure advantageously can allow determination of the appropriate size of prosthetic annuloplasty ring without needing multiple ring sizers, and without needing to insert and withdraw multiple ring sizers through a minimally invasive entry. Disclosed embodiments of such a ring sizer can generally include a dynamic, adjustable ring replica at the distal end of the ring sizer, with the ring replica being adjustable through a range of sizes corresponding to available prosthetic device sizes. A user can thus determine the appropriate size of annuloplasty ring for a particular patient or procedure using a single device, by manipulating the handle to adjust the size of the adjustable ring replica until the appropriate size is determined. Such adjustable ring sizers can be used in the repair of mitral and tricuspid valves, through both traditional surgical exposures as well as minimally invasive approaches. Some embodiments of a ring replica can be collapsed to fit through a small surgical incision.

Figure 3:
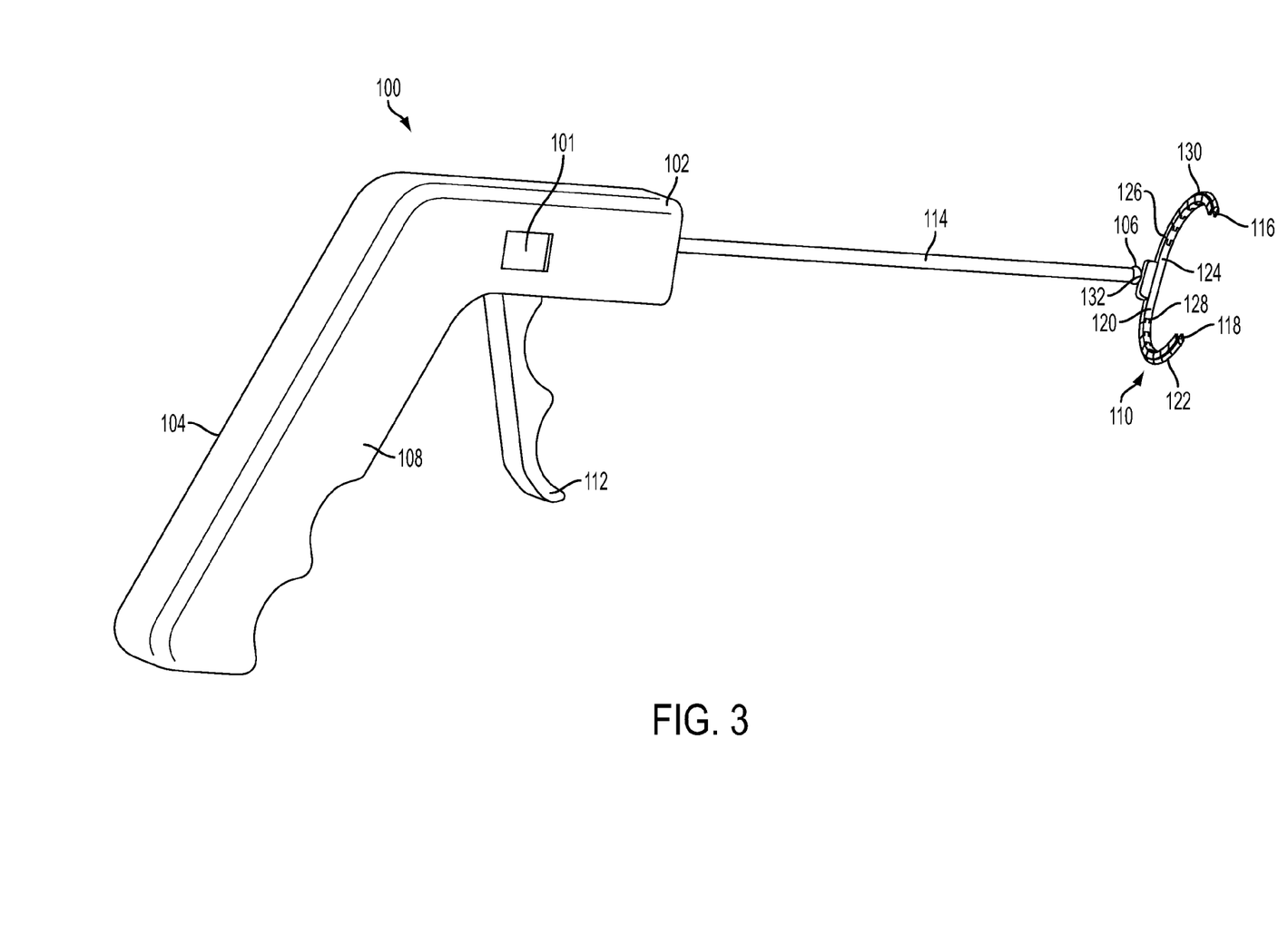
FIG. 3 is a perspective view of one embodiment of an adjustable annuloplasty ring sizer according to the present disclosure.

FIG. 3 shows one embodiment of a dynamic, adjustable ring sizer, or device, 100 for determining the appropriate size of prosthetic annuloplasty ring to use for a particular patient. The sizer 100 includes a device body 102, having a proximal end 104 and a distal end 106. The device body 102 can include a handle portion 108 adjacent the proximal end 104 and an adjustable C-shaped ring replica 110 adjacent the distal end 106. As will be explained in further detail below, the adjustable ring replica 110 can be configured to be adjusted to a plurality of different ring sizes corresponding to the available size range of prosthetic annuloplasty repair rings. For example, the adjustable ring replica 110 can expand and contract to larger or smaller overall diameters. In some embodiments, the ring replica 110 can expand and contract between a maximum, at-rest diameter corresponding to a 40 mm repair ring size and a minimum, contracted diameter corresponding to a 24 mm repair ring size, with the ring replica 110 being continuously adjustable through this range of sizes. Alternatively, in some embodiments, the adjustable ring sizer 100 can be configured so that it is adjustable in stepped increments, where each increment corresponds to an available repair ring size.

In use, the adjustable ring replica 110 can be positioned at or near an implant site (e.g., a patient's native mitral valve or tricuspid valve). Generally, manipulation of the sizer 100 can adjust the size of the adjustable ring replica 110 until the physician or other user has determined the appropriate size of prosthetic annuloplasty ring for a given procedure. A display window 101 positioned on the handle portion 108 can display the annuloplasty ring size corresponding to the present size of the ring replica 110. For example, in some embodiments, the display window 101 can be a digital display that displays a number corresponding to the appropriate size of annuloplasty ring determined by the sizer 100. In other embodiments, the display window 101 can simply be a string of numbers printed on the device that moves through the display window 101 as the adjustment trigger 112 is moved back and forth. Any suitable means for displaying the corresponding annuloplasty ring size can be used in connection with the present adjustable sizer; the above are meant as illustrative examples only.

In some embodiments, the display window 101 can be configured to provide the size of annuloplasty ring that corresponds to the present size of the adjustable ring replica 110. For example, if an embodiment of an adjustable ring sizer 100 has a ring replica size range corresponding to a repair ring size range of 24-40 mm, the display window 101 can be configured to read "24" or "24 mm" or the like, when the ring replica 110 is in its contracted, minimal configuration (e.g., when maximum tension is placed on the tension wires and the ring replica 110 is contracted to a size that corresponds to a repair ring size of 24). Likewise, the display window 101 can be configured to read "40" or "40 mm" or the like when the ring replica 110 is in its expanded, maximum configuration (e.g., when tension is released from the tension wires and the ring replica 110 is allowed to expand to a size that corresponds to a repair ring size of 40). The display window 101 can be configured to display the size within the range that corresponds to the present size of the ring replica 110. Thus, the display can change through a plurality of available repair ring sizes as the size of the ring replica 110 is adjusted (e.g., expanded and contracted via manipulation of the adjustment trigger 112) between the minimum and maximum configurations.

The sizer 100 can include an adjustment trigger 112 in connection with the handle portion 108. The adjustment trigger 112 can be configured to be positionable or movable between a first end position and a second end position, where movement of the adjustment trigger 112 between these endpoints (e.g., between the first end position and second end position) can result in adjustment of the size of the adjustable ring replica 110. In some embodiments, and as shown in FIG. 3, the adjustment trigger 112 can be a squeeze trigger, where the adjustment trigger 112 can be moved simply by squeezing or pulling it towards the handle portion 108 of sizer 100. In some embodiments, the adjustment trigger 112 can be movable from a first end position corresponding to a maximum, at-rest position (shown in FIG. 3) to a second end position corresponding to a minimum, contracted ring replica configuration. In some embodiments, the second end position can be a position where the adjustment trigger 112 is squeezed against the handle portion 108 of the sizer 100. For example, in some embodiments, the adjustment trigger can be movable from an at-rest position (shown in FIG. 3) to a position in contact with, or at least in close proximity to, the handle portion 108. Movement of the adjustment trigger 112 can be configured to adjust the size of the adjustable ring replica 110 as will be explained in further detail, below. In some embodiments, the adjustment trigger 112 can be moveable through a continuous range of positions. In other embodiments, the adjustment trigger 112 can be moveable through a series of incremental positions, where each position corresponds to a particular repair ring size. In alternative embodiments, the adjustment trigger 112 can be any suitable mechanism that can be used or configured to actuate or adjust the size of the ring replica 110.

A shaft 114 can couple the handle portion 108 to the adjustable ring replica 110. In some embodiments, shaft 114 is a malleable shaft that can allow for some flexibility. Such malleability can ease positioning of the adjustable ring replica 110 within a patient's body, especially for minimally invasive procedures. In some embodiments, the shaft 114 can have a hollow bore through the central axis of the shaft. The hollow bore can be configured to receive at least one elongated member configured to affect adjustment of the adjustable ring replica 110 to a plurality of different sizes. For example, one or more elongated members such as sutures, wire ropes, wires, and/or wire cable can pass through the bore of the shaft 114. In some embodiments, and as will be described in further detail below, the elongated members can continue through the shaft and into bores in the adjustable ring replica 110. In this manner, actuation, or movement of the adjustment trigger 112 can displace at least one elongate member, thereby contracting or expanding the size of the ring replica 110. For example, in one embodiment, squeezing the adjustment trigger 112 can displace a wire rope passing through the shaft 114, thereby causing contraction of the adjustable ring replica 110 to a smaller size. Releasing the adjustment trigger 112 can release tension on the elongate members, thereby allowing expansion of the adjustable ring replica 110 to a larger size. The adjustable ring replica 110 can thus be adjusted through a range of different sizes corresponding to available prosthetic annuloplasty ring sizes, by squeezing and releasing the adjustment trigger 112 until the appropriate size has been determined. In embodiments where the adjustable ring replica 110 is incrementally adjusted, the adjustable sizer 100 can include, for example, a ratcheting mechanism to incrementally contract the size of the adjustable ring replica 110. These embodiments can also include a release mechanism to allow expansion of the ring replica 110 to larger sizes.

Figure 4:
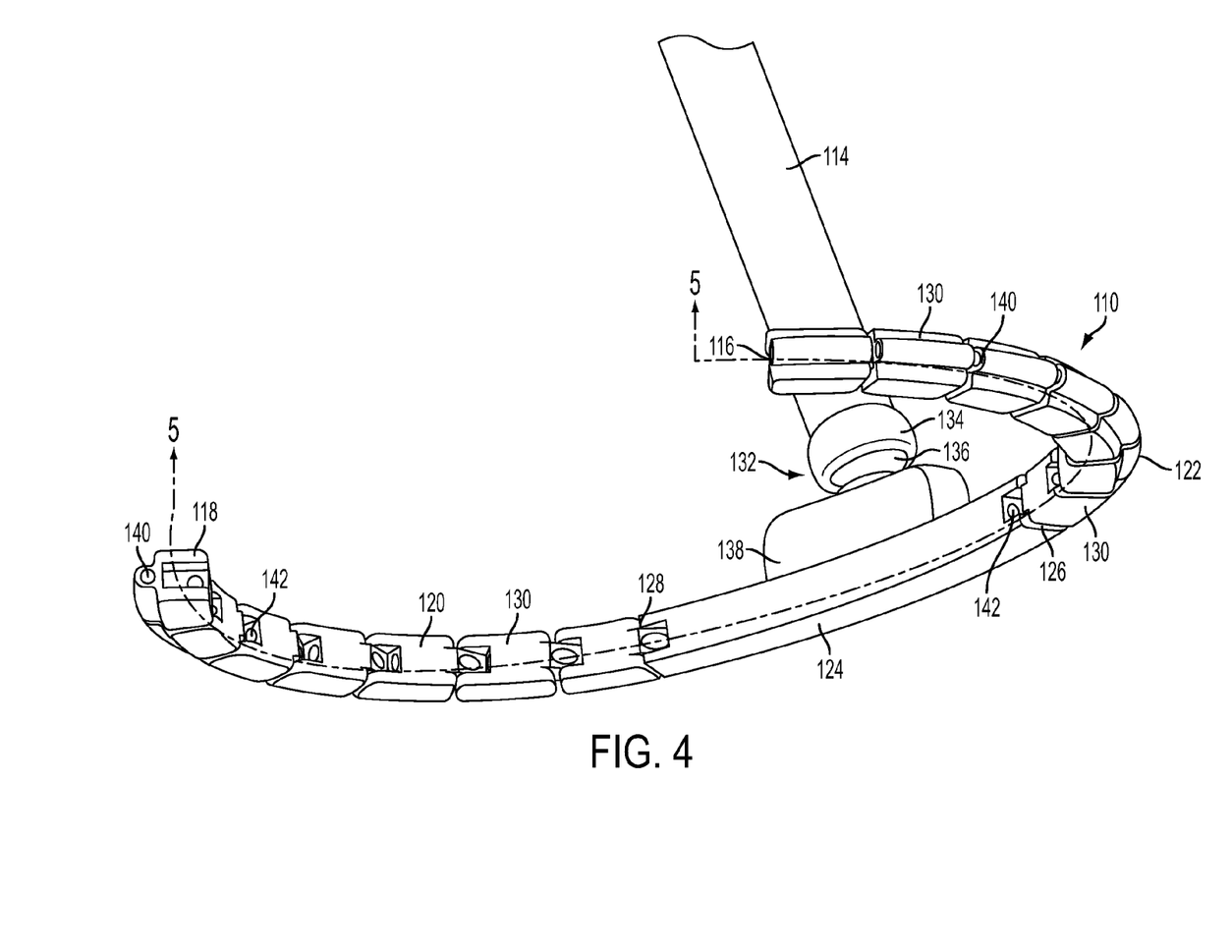
FIG. 4 shows a perspective, close-up view of the adjustable ring replica shown on the adjustable annuloplasty ring sizer of FIG. 3.

The adjustable ring replica 110 can be generally C-shaped, with a first free end 116 and a second free end 118. As the size of the ring replica 110 is adjusted, the first and second free ends 116, 118 can be configured to move closer together and farther apart as the ring replica 110 is adjusted to smaller and larger sizes, respectively. As best seen in FIG. 4, the ring replica 110 can have an inner ring surface 120 defined by the interior of the C-shape, and an outer ring surface 122 defined by an exterior of the C-shape.

In some embodiments, the adjustable ring replica 110 can include a number of different individual pieces that can move with respect to one another, thereby allowing adjustment of the ring replica's size. In one specific embodiment, the adjustable ring replica 110 can include a centrally located, elongated, curved backbone segment 124 and a plurality of articulating segments 130 extending from a first backbone end 126 and a second backbone end 128 towards the first free end 116 and the second free end 118, respectively, of the ring replica 110. Thus, a plurality of articulating segments 130 can be serially arranged and coupled to one another and extend in an elongated manner from the first backbone end 126 to the first free end 116 of the ring replica 110. Similarly, a plurality of articulating segments 130 can be serially arranged and coupled to one another and extend in an elongated manner from the second backbone end 128 to the second free end 118 of the ring replica 110. Thus, the backbone segment 124 can be positioned as a central portion of the ring replica 110, being positioned approximately equidistant from the first and second free ends 116, 118 of ring replica 110.

The articulating segments 130 can be configured to engage with one or more adjacent articulating segment(s) 130 and/or the backbone segment 124. The articulating segments 130 can be configured such that when they are engaged with each other and the backbone segment 124, they form arcs, or curved segments, extending from the first and second backbone ends 126, 128. The articulating segments 130 can be moveable with respect to one another, and with respect to the backbone segment 124. In this manner, an adjustable ring replica 110 is formed, whereby movement of the articulating segments 130 can effectively adjust the overall size of the ring replica 110 to determine the best size of annuloplasty ring for a particular patient or procedure.

The adjustable ring replica 110 can be coupled to the malleable shaft 114 in order to allow manipulation of the handle portion 108 to adjust the size of the ring replica 110. In some embodiments, the ring replica 110 can be coupled to the shaft 114 via an articulating joint 132. Articulating joint 132 can be, for example, a ball and socket joint that can be configured to allow a low-friction, full range of motion of the ring replica 110 with respect to the shaft 114. Articulating joint 132 can be configured to allow the ring replica 110 to pivot in all directions with respect to the shaft 114, in order to allow proper positioning of the ring replica when in use in vivo. In the specific embodiment shown in FIG. 4, the articulating joint 132 can be composed of a socket 134 positioned adjacent the distal end of shaft 114 and a ball portion 136 which can be coupled to the backbone segment 124, such as by joint connection 138. In some embodiments, joint connection 138 and ball portion 136 can be formed of an integral body, with the joint connection 138 coupled to the backbone segment 124, such as by screws or other fasteners. In other embodiments, articulating joint 132 can be any other suitable joint that can provide enough range of motion to allow proper positioning of the ring replica 110 when the adjustable ring sizer 100 is in use.

Figure 5:
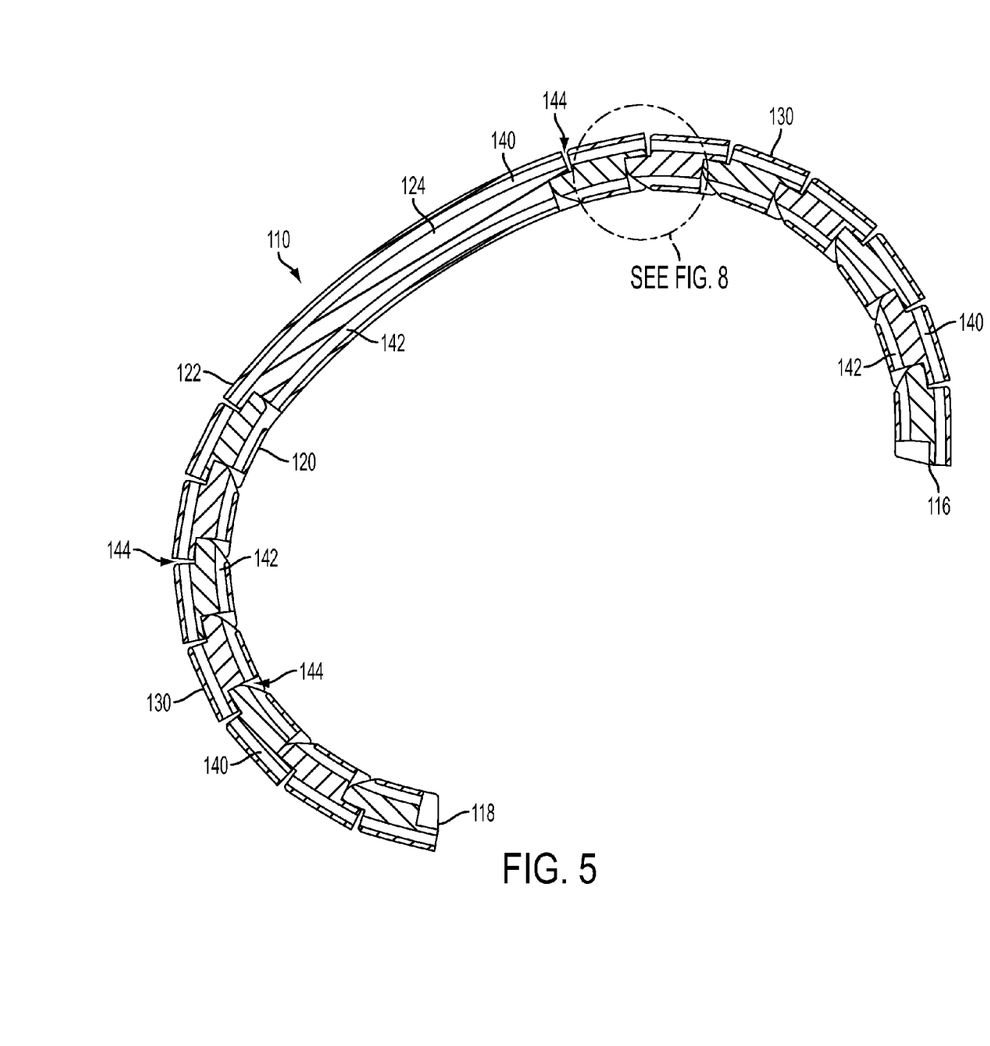
FIG. 5 shows a cross section view of the adjustable ring replica of FIG. 4, taken along line 5-5 in FIG. 4.

In some embodiments, adjustment of the size of the ring replica 110 (e.g., manipulation of the articulating segments 130) can be provided via one or more elongated members that pass through the shaft 114 as well as through channels in the backbone segment 124 and articulating segments 130. As best seen in FIG. 5, which shows a cutaway cross-section view of the ring replica 110 shown in FIGS. 3-4, some embodiments of a ring replica 110 can include two bores, or channels 140, 142, to receive such elongated members. As shown in FIG. 5, the channels 140, 142 can extend essentially continuously from the first free end 116 to the second free end 118 of the ring replica 110. The channels 140, 142 can be hollow bores that extend through the interior, along the longitudinal axis of the elongated backbone segment 124 (see longitudinal axis L2 in FIG. 11) as well as each of the articulating segments 130 (see longitudinal axis L1 in FIG. 9), thereby being configured to receive one or more elongated members. In some configurations of the ring replica 110, small gaps, or spaces 144 may form between adjacent articulating segments 130 or between an articulating segment 130 and the backbone segment 124. Elongated members that pass through the channels 140, 142 can simply extend across these gaps 144, and continue on through the respective channel 140, 142 in the next adjacent articulating segment 130. One or more of the elongated members can extend through one or more of the channels 140, 142 from the first free end 116 to the second free end 118 of the ring replica 110.

In some embodiments, the ring replica 110 can have an extension wire channel 140 positioned adjacent the outer surface 122 of the ring replica 110, and a tension wire channel 142 positioned adjacent the inner surface 120 of the ring replica 110. In some embodiments, elongated members (e.g., sutures, wire rope, or wire cable) that pass through the extension wire channel 140 and tension wire channel 142 can effectively hold together the backbone segment 124 and the articulating segments 130 to form the ring replica, without the need for fasteners or adhesives joining adjacent articulating segments 130, thereby allowing for a flexible configuration, and movement of the articulating segments 130 with respect to one another.

The extension wire channel 140 can be configured to receive a single elongated member, or extension wire (see, e.g., extension wire 146 in FIG. 6), that extends from the first free end 116 to the second free end 118 of the ring replica 110. The extension wire can extend through the extension wire channel 140 of each articulating segment 130 and the backbone segment 124, spanning the gaps or spaces 144. The extension wire can be any elastically deformable material that can impart at least a minimal bending stiffness to the ring replica 110. In some embodiments, the extension wire can be a flexible wire, such as a Nitinol wire. The extension wire can be configured to have enough stiffness to give an initial, at-rest shape to the ring replica 110 (e.g., the shape of the ring replica 110 corresponding to its largest size in the adjustment range), yet flexible enough to allow contraction or compression of the ring replica 110 (e.g., reduction in the overall diameter of the ring replica 110, through the range of sizes) in response to action on the tension wires. The extension wire can be configured to provide a bias or shape-memory properties, such that when tension is placed on the tension wires, the ring replica 110 can be adjusted to smaller sizes and when tension is released from the tension wires, the extension wire can force the ring replica 110 back to the maximum, at-rest ring size.

While the extension wire is typically a single, elongated wire member, the tension wire channel 142 (typically positioned adjacent the inner surface 120 of ring replica 110) can be configured to receive two elongated members, or tension wires. A first tension wire can extend from the backbone segment 124 to the first free end 116 of the ring replica 110, and a second tension wire can extend from the backbone segment 124 to the second free end 118 of the ring replica 110. Applying tension to the tension wires (such as via displacing them by manipulating or actuating the adjustment trigger 112 of handle portion 108 (see FIG. 3)) can exert force on the articulating segments 130, moving them with respect to one another, and bringing the first and second free ends 116, 118 of ring replica 110 closer together, to effectively reduce the size of the ring replica 110. In this manner, the ring replica 110 is adjustable through a range of sizes and can be varied continuously or incrementally from a maximum, at-rest size imparted by the extension wire, to a minimum, contracted size when acted on by the tension wires.

The tension wires can be, for example, a flexible wire rope, a wire cable, a braided wire cable, sutures, strings, or any material with sufficient flexibility and tensile strength to allow for adjustment of the ring replica 110 according to the present disclosure. In some embodiments, the tension wires can have low bending stiffness but high tensile strength. The tension wires can be flexible, thereby allowing movement of the articulating segments 130 with respect to one another. In one specific embodiment, the tension wires can be, for example, stainless steel wire rope.

In some embodiments, each of the articulating segments 130 can be identical to one another. In other embodiments, one or more of the articulating segments 130 can be slightly different from each of the other articulating segments 130. For example, in some embodiments of an adjustable ring sizer, having the tension channel 142 in a slightly different location from segment to segment can change the lever arms acting on the respective articulating segments 130, and therefore the amount of actuation for a respective articulating segment for a given change in tension in the tension wire. This can allow the shape of the ring replica 110 to change as the ring size is adjusted.

Figure 6:
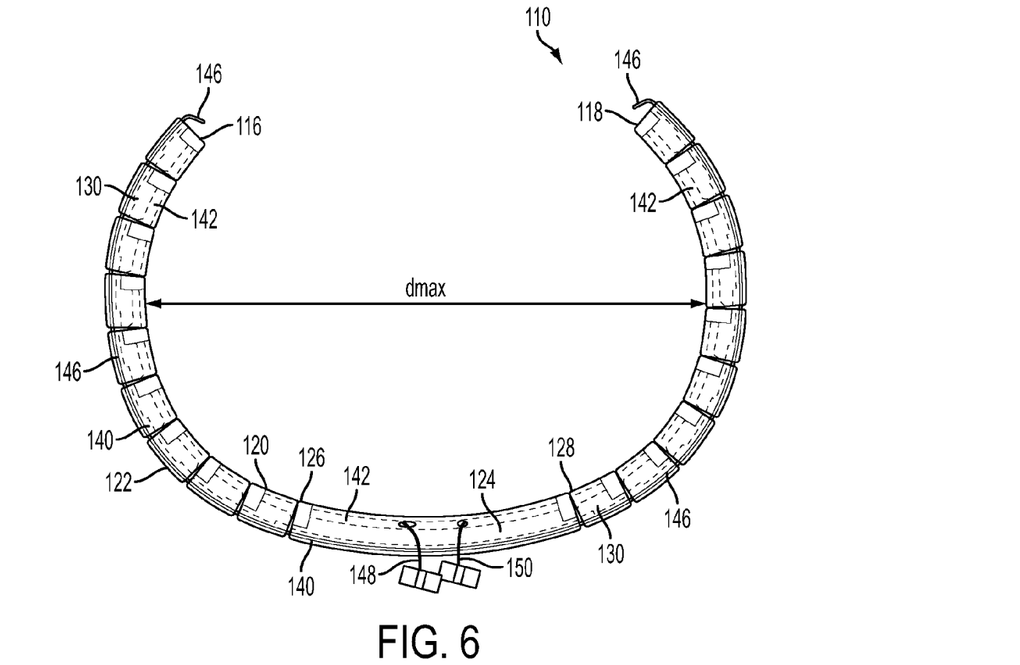
FIG. 6 shows a top plan view of one embodiment of an adjustable ring replica, in an expanded configuration.
Figure 7:
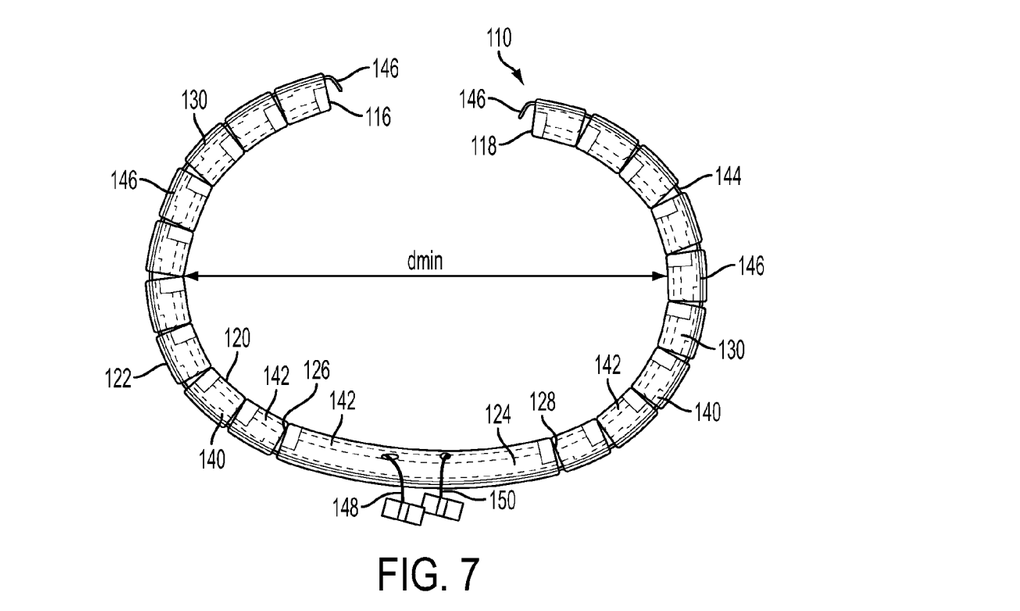
FIG. 7 shows a top plan view of one embodiment of an adjustable ring replica, in a contracted configuration.

FIGS. 6 and 7, which are not drawn to scale, show one example of the relative range of sizes for one embodiment of an adjustable ring replica 110 according to the present disclosure. The ring replica 110 is shown in an at-rest, maximum ring size in FIG. 6, having a maximum diameter of $d_{max}$, and is shown in a smaller ring size in FIG. 7, having a maximum diameter of $d_{min}$, where $d_{min}$ is smaller than $d_{max}$. The ring replica 110 can be adjustable continuously or incrementally between the maximum and minimum ring sizes, to allow a physician or other user to adjust the ring replica 110 to a plurality of ring sizes corresponding to available annuloplasty repair ring sizes, in order to best determine the appropriate annuloplasty ring prosthesis to use for a particular patient or procedure. Relaxing the tension wires can allow the ring replica 110 to expand to the enlarged configuration shown in FIG. 6, while tensioning the tension wires can force the ring replica 110 to be contracted to the smaller configuration shown in FIG. 7.

In the embodiment shown in FIGS. 6 and 7, an adjustable ring replica 110 is formed from a backbone segment 124 having a first backbone end 126 and a second backbone end 128. A plurality of articulating segments 130 engage with one another and extend serially from the first backbone end 126 to the first free end 116 of the ring replica 110. Similarly, a plurality of articulating segments 130 engage with one another and extend serially from the second backbone end 128 to the second free end 118 of the ring replica 110. An extension wire channel 140 (shown dashed) extends through the backbone segment 124 and each articulating segment 130, adjacent the outer surface 122 of the ring replica 110. The extension wire channel 140 is configured to receive an elongated member, extension wire 146, which extends from the first free end 116 to the second free end 118 of the ring replica 110. The extension wire 146 can be secured in any suitable manner so that it remains in place within the extension wire channel 140. For example, in some embodiments, the ends of the extension wire 146 can be fastened or adhered to the first and second free ends 116, 118, respectively of the ring replica 110, such as by welding, adhesives, or some other fastener. In some embodiments, the ends of the extension wire can simply be enlarged, knotted, twisted, bent, or otherwise secured so that the extension wire 146 cannot be pulled through the extension wire channel 140. For clarity, FIGS. 6 and 7 show the articulating segments 130 and backbone segment 124 in transparent material so that extension wire 146 is visible throughout the ring replica 110.

A tension wire channel 142 (shown dashed) extends through the backbone segment 124 and each articulating segment 130, adjacent the inner surface 120 of the ring replica 110. The tension wire channel 142 is configured to receive one or more elongated members, such as tension wires 148, 150. Tension wire 148 extends through the tension channel 142 from the first free end 116 of the ring replica 110, through a plurality of articulating segments 130, through a portion of the backbone segment 124, and further through the malleable shaft and handle portion of the adjustable ring sizer (although for clarity, the tension wires 148, 150 are not drawn inside the tension channel 142, and are shown capped in FIGS. 6 and 7). Similarly, tension wire 150 extends through the tension channel 142 from the second free end 118 of the ring replica 110, through a plurality of articulating segments 130, through a portion of the backbone segment 124, and further through the malleable shaft and handle portion of the adjustable ring sizer. The extension wire 146 and tension wires 148, 150, span any gaps 144 between adjacent articulating segments 130 and/or between the backbone segment 124 and adjacent articulating segments 130.

The extension wire 146 runs through the outer extension channel 140 and can be configured to hold the ring replica 110 at the maximum ring size (e.g., $d_{max}$ shown in FIG. 6) when there is no tension on the tension wires 148, 150. The tension wires 148, 150 (e.g., flexible wire rope cables) run through the inner tension wire channel 142. Tensioning the tension wires 148, 150 (e.g., by pressing or squeezing the adjustment trigger 112 on handle portion 108 shown in FIG. 3) creates a moment about a pivot area, which in turn causes flexion of the joint formed by adjacent articulating segments 130. Each articulating segment can have a male and female articulating area that act as a hinge and allow the two segments to flex (e.g., applying tension to the tension wires 148, 150 can cause adjacent articulating segments to articulate at the pivot area formed where respective male and female articulating areas of adjacent articulating segments interface with one another).

Figure 8:
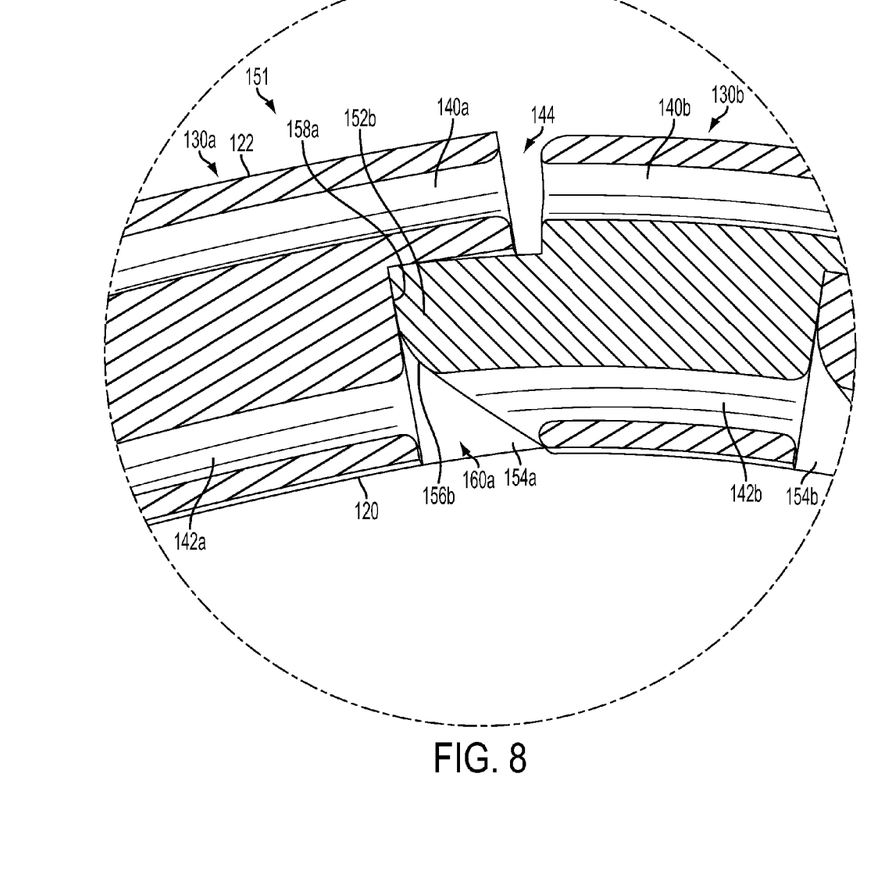
FIG. 8 is a cross-section, close-up view of a portion of FIG. 5, showing two articulating segments engaged with one another.
Figure 9:
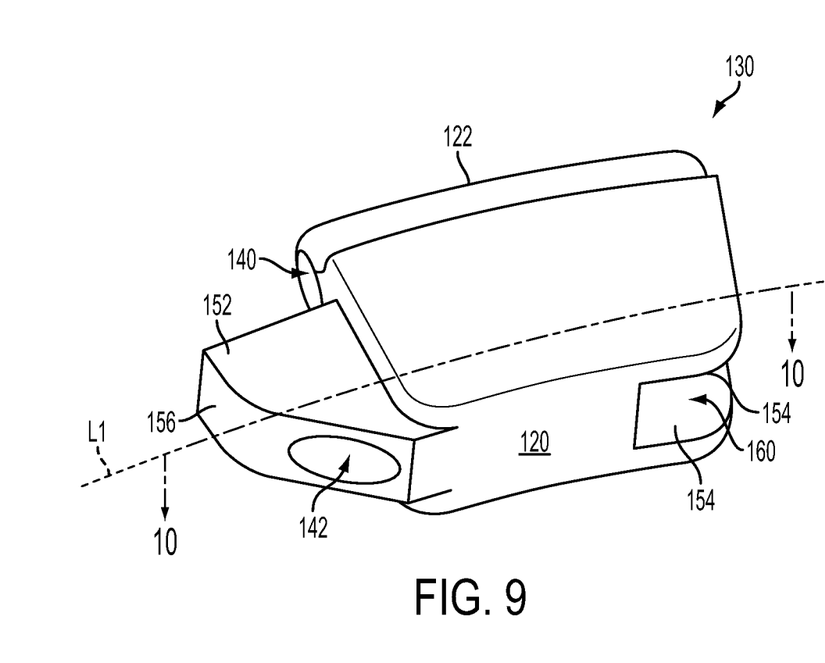
FIG. 9 is a perspective view of one embodiment of an articulating segment that can be used to create an adjustable annuloplasty ring replica according to the present disclosure.

FIG. 8 shows a close-up, cross-section view of such a joint 151 formed by two adjacent articulating segments 130a, 130b. As shown in FIG. 8, adjacent articulating segments 130a, 130b, engage with one another such that a pivot area is formed at the interface between a pivoting projection 152b (male articulating area) of articulating segment 130b and a receiving area 160a (female articulating area) of articulating segment 130a. The pivoting projection 152b can be inserted into receiving space 160a formed by a pair of receiving surfaces 154a (receiving space 160 is best seen in FIG. 9; only one receiving surface 154a is visible in FIG. 8). A pivot surface 156b of articulating segment 130b can engage with and pivot against pivot face 158a of articulating segment 130a. Tensioning the tension wires (which are not shown in FIG. 8, but would extend through tension wire channel 142, (e.g., the portions 142a, 142b, of tension wire channel 142 that extend through articulating segments 130a, 130b, respectively) creates a moment about the pivot area that in turn causes flexion of the joint 151 (e.g., movement of articulating segments 130a, 130b with respect to one another that increases or decreases the size of gap 144). As the articulating segments 130a, 130b, move with respect to one another, the pivot surface 156b pivots against pivot face 158a, and the pivoting projection 152b can move within the receiving space 160a (e.g., against receiving surfaces 154a). The degree of flexion of the joint 151 is related to the amount of tension (e.g., displacement) placed on the tension wires in the tension channel 142. As described in more detail above, one tension wire can extend through each half of the ring replica, and each of the two tension wires can extend through a portion of the backbone segment, through the malleable shaft, and can terminate at the trigger mechanism in the handle. Actuation of the adjustment trigger can cause a displacement of the tension wires and therefore actuation between each of the articulating segments 130 (e.g., articulating segments 130a, 130b) of a ring replica.

Figure 10:
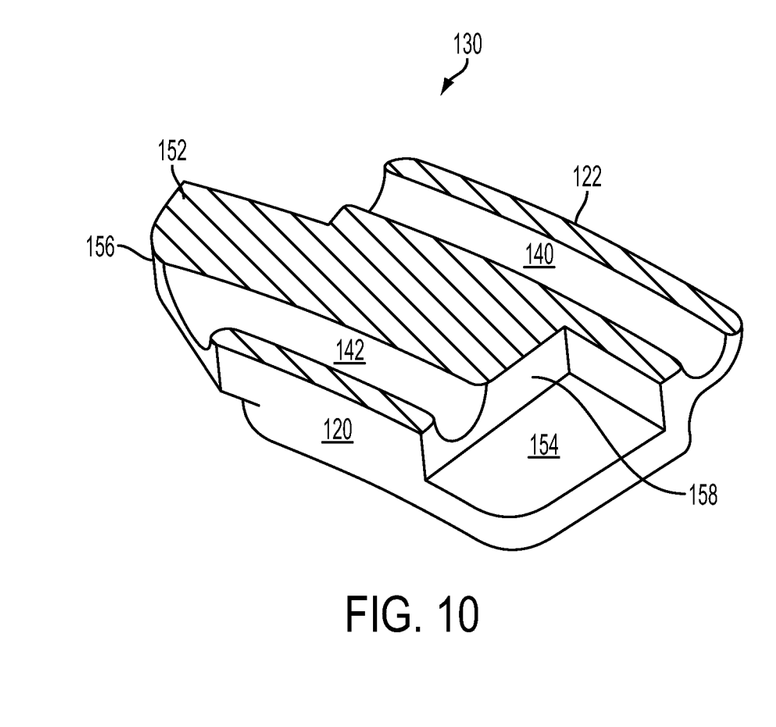
FIG. 10 is a cross-section view of the articulating segment of FIG. 9, taken along line 10-10 in FIG. 9.

Turning now to a single articulating segment 130, FIG. 9 shows a perspective view of a single articulating segment 130, and FIG. 10 shows a cut-away perspective view of the articulating segment 130 of FIG. 9. Extension wire channel 140 is visible, adjacent to the outer surface 122 of the ring replica, and tension wire channel 142 is positioned adjacent to the inner surface 120 of the ring replica. A pivoting projection 152 can be positioned at one end of the articulating segment, and a receiving space 160 can be positioned at the opposite end of the articulating segment, the receiving space 160 being defined by a first and second receiving surface 154. Thus, the pivoting projection 152 can be configured to engage with the receiving space of a first adjacent articulating segment and similarly, the receiving space 160 can be configured to receive a pivoting projection from a second adjacent articulating segment. Each pivoting projection 152 can include a pivot surface 156 which can be configured to pivot against the pivot face 158 within the receiving space 160 (see FIG. 10). In this manner, when tension is placed on the tension wires within the tension channel 140, flexion between adjacent articulating segments 130 can be created via the pivoting projection 152 moving against the receiving face 158 and receiving surfaces 154 within the receiving space 160.

The articulating segments 130 can be composed of any suitable material that can be configured as described above. In some embodiments, the articulating segments can be formed of a molded polymer such as polycarbonate or ABS.

In some embodiments, each articulating segment of the ring replica can be identical in a given sizer device. In other embodiments, the relative locations of the tension wire channel and the pivot area can be adjusted from segment to segment to control how the shape of the ring replica changes as it is adjusted from the largest to the smallest size. This can accommodate changes in shape of the repair rings as the size changes, such as with the commercially available Carpentier-Edwards Physio II Annuloplasty Ring for mitral valve repair (Edwards Lifesciences Corp, Irvine, Calif.), which evolves from the native D-shape to a more circular shape as the repair ring size increases from 24 to 40, to accommodate the pathological changes in mitral annular dimensions. To accommodate these changes, in some embodiments of an adjustable ring sizer, having the tension channel in a slightly different location relative to the pivot area from segment to segment can change the lever arms accordingly, and therefore the amount of actuation for a respective articulating segment for a given change in tension in the tension wire. This can allow the shape of the ring replica to change as the size is adjusted.

Figure 11:
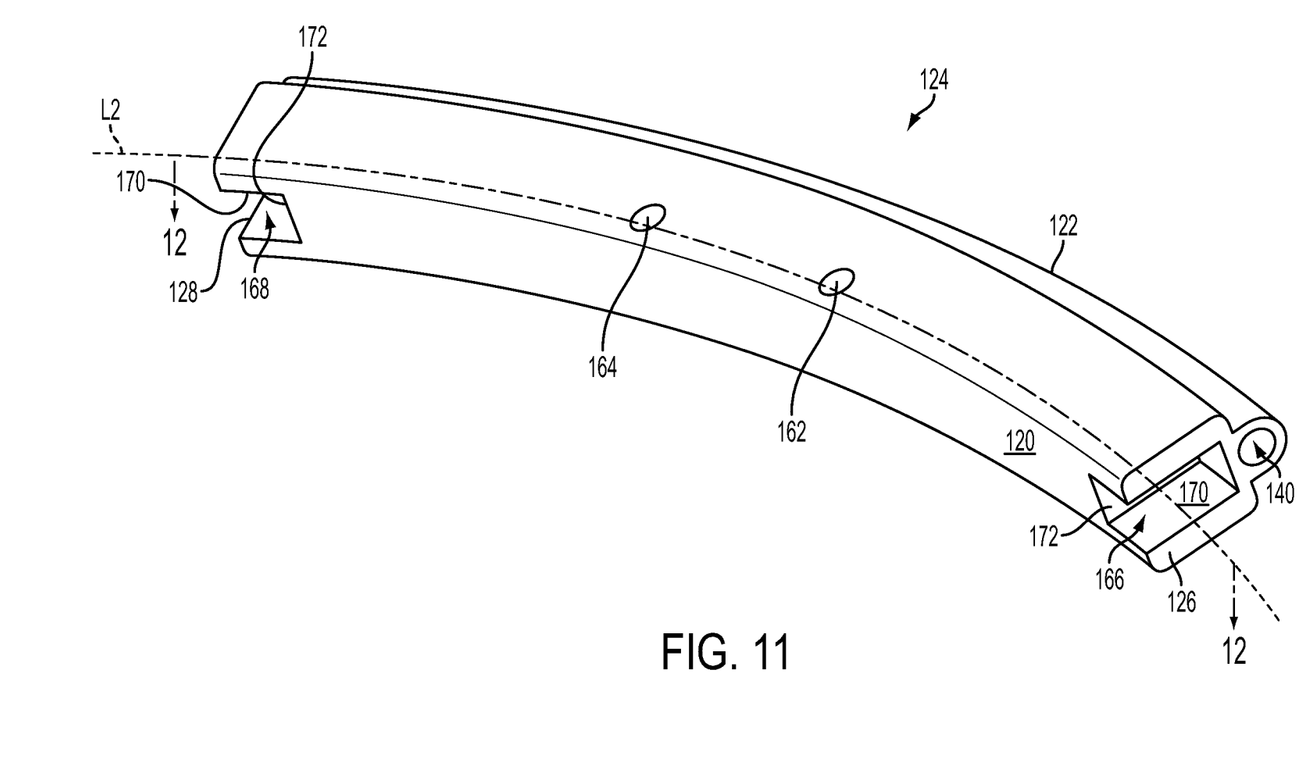
FIG. 11 shows one embodiment of a backbone segment that can form a central portion of an adjustable ring replica according to the present disclosure.
Figure 12:
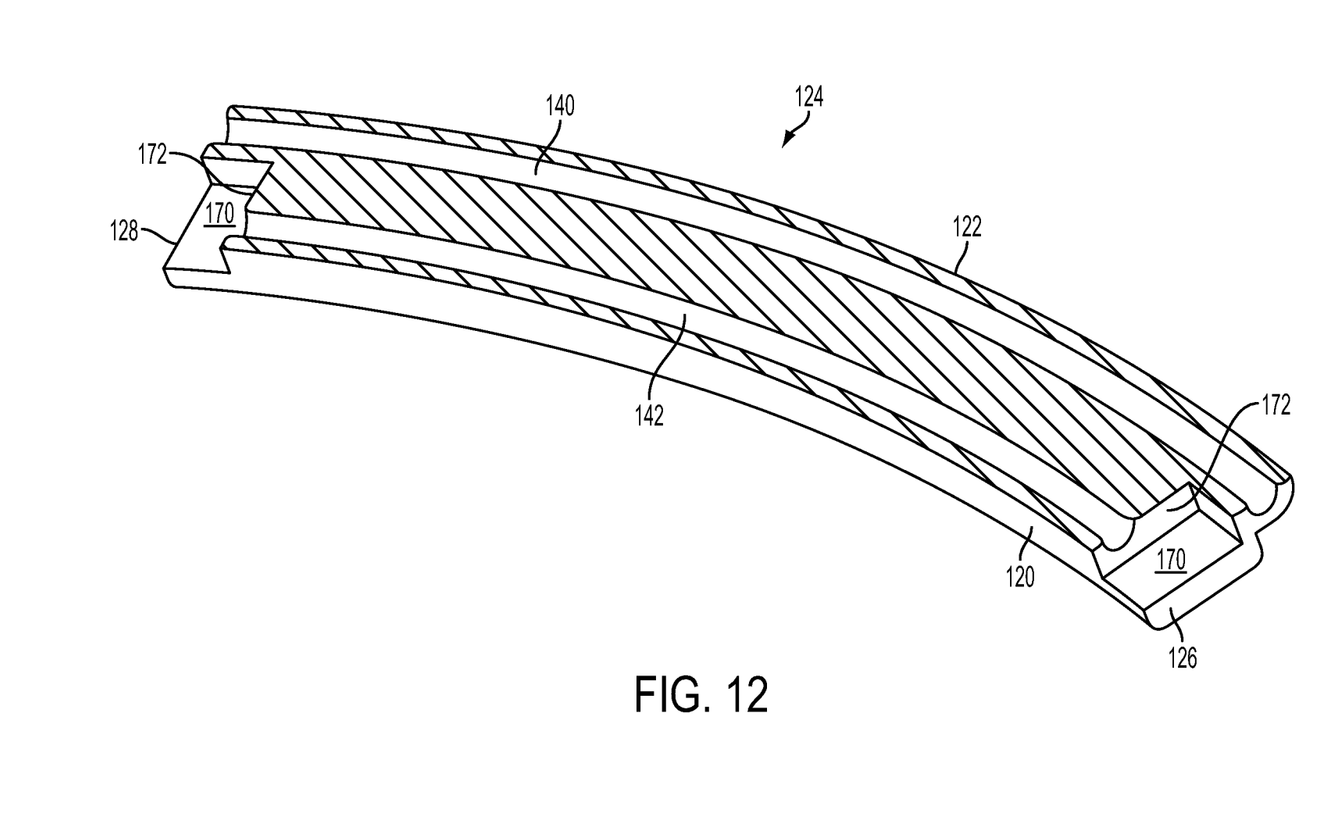
FIG. 12 is a cross-section view of the backbone segment of FIG. 11, taken along line 12-12 in FIG. 11.

FIGS. 11 and 12 show a perspective view and a cut-away view of backbone segment 124, respectively. In contrast to the embodiment of the articulating segment 130 shown in FIGS. 9 and 10, the backbone segment 124 of FIGS. 11 and 12 can be symmetrical, with both the first backbone end 126 and the second backbone end 128 having receiving spaces 166, 168, respectively. Each receiving space 166, 168 can be defined by opposing receiving surfaces 170 and a receiving face 172. The first and second receiving spaces 166, 168 can be configured to receive respective pivoting projections from a first and second articulating segment that engage with the backbone segment 124, such that the pivot surface of the pivoting projection of each respective adjacent articulating segment engages with the respective receiving face 172 of the backbone segment 124.

An extension wire (not shown, for clarity) can extend through the extension channel 140 adjacent the outer surface 122 of the ring replica. A first and second tension wire (not shown, for clarity) can extend through approximately half of the ring replica. Each tension wire can extend through a portion of the tension wire channel 142 adjacent the inner surface 120 of the backbone segment 124 and through the tension wire channel of a plurality of articulating segments (e.g., each tension wire can extend through the tension wire channel of half of the articulating segments, as each tension wire extends through a portion of the backbone segment to one free end of the ring replica). When tension is placed on the tension wire, a moment is created about the pivot areas where pivoting projections of adjacent articulating segments interface with the receiving spaces 166, 168 of the backbone segment, thereby causing flexion (e.g., movement of the articulating segments with respect to the backbone segment 124). In this manner, tension on the tension wires can adjust the ring size of the ring replica.

Backbone segment 124 can also include first and second tension wire entrance bores 162, 164 (FIG. 11). The entrance bores 162, 164 can be configured to receive a first and second tension wire. In some embodiments of a dynamically adjustable ring sizer according to the present disclosure, each respective tension wire can extend through a malleable shaft coupling the handle portion to the ring replica, through the respective first or second entrance bores 162, 164, and into a portion of the tension channel 142 of backbone segment 124. The first tension wire can extend through the first entrance bore 162, through a portion of the tension wire channel 142 towards the first backbone end 126, and then through each of a plurality of serially arranged articulating segments to the first free end of the ring replica. Similarly, the second tension wire can extend through the second entrance bore 164, through a portion of the tension wire channel 142 towards the second backbone end 128, and then through each of a plurality of serially arranged articulating segments to the second free end of the ring replica.

As with the articulating segments, the backbone segment 124 can be composed of any suitable material that can be configured as described above. In some embodiments, the backbone segment can be formed of a molded polymer such as polycarbonate or ABS.

Presently disclosed embodiments of an adjustable ring sizer can provide several advantages over conventional repair ring sizers. For example, in some embodiments, the adjustability of the present dynamic ring sizers can allow a single sizing device to cover the entire range of available repair rings. By contrast, in conventional methods, one would work with several different static ring sizers, one static sizer corresponding to each available size of repair ring. In some embodiments, the use of a single adjustable sizer according to the present disclosure (instead of multiple, static sizers) can reduce clutter in the operating field, make sizing the patient's annulus quicker, and/or reduce bypass time during repair procedures.

Furthermore, some embodiments of an adjustable ring sizer according to the present disclosure can be configured to collapse, thereby facilitating minimally invasive surgical procedures, which are performed through small surgical incisions. By contrast, conventional static sizers can be too large to fit through a minimally invasive surgical incision.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. I therefore claim as my invention all that comes within the scope and spirit of these claims.

I claim:

1. A sizing device, comprising:
a device body having a proximal end and a distal end;
a handle portion positioned adjacent the proximal end of the device body;
an adjustable annuloplasty ring replica positioned adjacent the distal end of the device body, wherein the adjustable annuloplasty ring replica is configured to be adjusted to a plurality of different sizes, and wherein the adjustable annuloplasty ring replica comprises a generally C-shaped ring replica having a first free end and a second free end, as well as an inner surface and an outer surface; and
a shaft that couples the adjustable annuloplasty ring replica to the handle portion.

2. The device according to claim 1, wherein the shaft is a malleable shaft comprising a hollow bore configured to receive at least one elongated member configured to adjust the adjustable annuloplasty ring replica to a plurality of different sizes.

3. The device according to claim 2, wherein the handle portion comprises an adjustment trigger, wherein actuation of the adjustment trigger is configured to expand and contract the adjustable annuloplasty ring replica.

4. The device according to claim 3, wherein actuation of the adjustment trigger displaces the at least one elongated member.

5. The device according to claim 2, wherein the at least one elongated member comprises at least one selected from the following: suture, wire rope, and wire cable.

6. The device according to claim 1, wherein the adjustable annuloplasty ring replica comprises an extension wire channel and a tension wire channel.

7. The device according to claim 6, wherein the extension wire channel is positioned adjacent the outer surface of the adjustable ring replica, and the tension wire channel is positioned adjacent the inner surface of the adjustable ring replica.

8. The device according to claim 7, wherein the extension wire channel is configured to receive at least one elongated member.

9. The device according to claim 8, wherein the at least one elongated member comprises an elastically deformable material and extends from the first free end of the adjustable ring replica to the second free end of the adjustable ring replica.

10. A device comprising:
a handle portion positioned adjacent a proximal end of the device;
an adjustable C-shaped annuloplasty ring replica positioned adjacent a distal end of the device, wherein the adjustable C-shaped annuloplasty ring replica comprises a first free end and a second free end;
a malleable shaft coupling the handle portion to the adjustable C-shaped annuloplasty ring replica via an articulating joint, the malleable shaft being configured to receive at least one tension wire; and
an adjustment trigger positioned adjacent the handle portion, wherein actuation of the adjustment trigger is configured to displace the at least one tension wire, and wherein displacement of the at least one tension wire is configured to contract and/or expand the adjustable C-shaped annuloplasty ring replica;
wherein the C-shaped adjustable annuloplasty ring replica comprises a backbone segment coupled to the malleable shaft, wherein the backbone segment comprises a first backbone end and a second backbone end opposite the first backbone end, wherein a first plurality of articulating segments serially coupled to one another extend in an elongated manner from the first backbone end to the first free end of the ring replica, and wherein a second plurality of articulating segments serially coupled to one another extend in an elongated manner from the second backbone end to the second free end of the ring replica, wherein the C-shaped adjustable annuloplasty ring replica comprises an extension wire channel adjacent an outer ring surface and a tension wire channel adjacent an inner ring surface, and wherein displacement of the at least one tension wire is configured to move each respective articulating segment with respect to each adjacent articulating segment and/or the backbone segment.

11. The device according to claim 10, further comprising a display on the handle portion of the device, wherein the display is configured to provide the size of annuloplasty ring that corresponds to each respective size of the adjustable annuloplasty ring replica.

12. The device according to claim 11, further comprising an extension wire that extends through the extension wire channel from the first free end to the second free end of the C-shaped annuloplasty ring replica.

13. A sizing device, comprising:
a device body having a proximal end and a distal end;
a handle portion positioned adjacent the proximal end of the device body;
an adjustable annuloplasty ring replica positioned adjacent the distal end of the device body, wherein the adjustable annuloplasty ring replica is configured to be adjusted to a plurality of different sizes, wherein the adjustable annuloplasty ring replica comprises a plurality of articulating segments each moveable with respect to one or more respective adjacent articulating segment, wherein the adjustable annuloplasty ring replica comprises an elongated backbone segment having a first backbone end and a second backbone end, wherein a first plurality of articulating segments are serially arranged and coupled to the first backbone end and extend to the first free end of the adjustable ring replica, and a second plurality of articulating segments are serially arranged and coupled to the second backbone end and extend to the second free end of the adjustable ring replica; and
a shaft that couples the adjustable annuloplasty ring replica to the handle portion.

14. The device according to claim 13, wherein the elongated backbone segment is coupled to the shaft.

15. The device according to claim 14, wherein the elongated backbone segment is coupled to the shaft via an articulating joint.

16. The device according to claim 13, wherein the adjustable ring replica comprises an extension wire channel and a tension wire channel.

17. The device according to claim 16, wherein the tension wire channel is configured to receive at least one elongated member.

18. The device according to claim 13, wherein the adjustable annuloplasty ring replica comprises a generally C-shaped ring replica.

19. The device according to claim 1, wherein the adjustable annuloplasty ring replica comprises a plurality of articulating segments serially arranged and hinged with respect to one or more respective adjacent articulating segment, and the sizing device further includes at least one tension wire extending along the shaft from the handle portion to the adjustable annuloplasty ring replica and configured to contract and/or expand the adjustable C-shaped annuloplasty ring replica by pivoting the articulating segments respect to the adjacent articulating segments.

\* \* \* \* \*